United States Patent [19]

Ritzl

[11] Patent Number: 4,524,303
[45] Date of Patent: Jun. 18, 1985

[54] GLOW DISCHARGE TUBE FOR SPECTRAL-ANALYTICAL TESTS

[76] Inventor: Hermann Ritzl, Hauptstrasse 60, 8031 Seefeld 2, Fed. Rep. of Germany

[21] Appl. No.: 500,712

[22] Filed: Jun. 3, 1983

[30] Foreign Application Priority Data

Jun. 4, 1982 [DE] Fed. Rep. of Germany ....... 3221274

[51] Int. Cl.³ .............................................. H01J 7/24
[52] U.S. Cl. .............................. 315/111.81; 315/110; 313/619
[58] Field of Search .................... 315/109, 110, 111.11, 315/111.81, 237.5; 313/619

[56] References Cited

U.S. PATENT DOCUMENTS 3,566,304  2/1971  Neusel et al. ................... 315/110 X

OTHER PUBLICATIONS

M. G. Zakharchenko et al., A Stabilisation Unit for a Cold Cathode Glow Discharge Electron-Beam Gun, 12/75, p. 56, Automatic Weld., (GB) vol. 28 #12.

Primary Examiner—David K. Moore
Attorney, Agent, or Firm—Jones, Tullar & Cooper

[57] ABSTRACT

A glow discharge tube for emission spectral analysis is disclosed. The tube includes an anode cavity which is connected on one side to a carrier gas source and is connected on the other side to a first vacuum pump. The anode cavity is in communication, by way of a restrictor, with a cathode cavity which is connected to a second vacuum pump. The second pump produces a vacuum that is greater than that produced by the first pump. To reduce the margin of error in the accuracy of spectral-analytical tests, the gas pressure in the main cavity is maintained at a constant value by an electronic control which regulates the amount of carrier gas being fed to the anode cavity.

9 Claims, 1 Drawing Figure

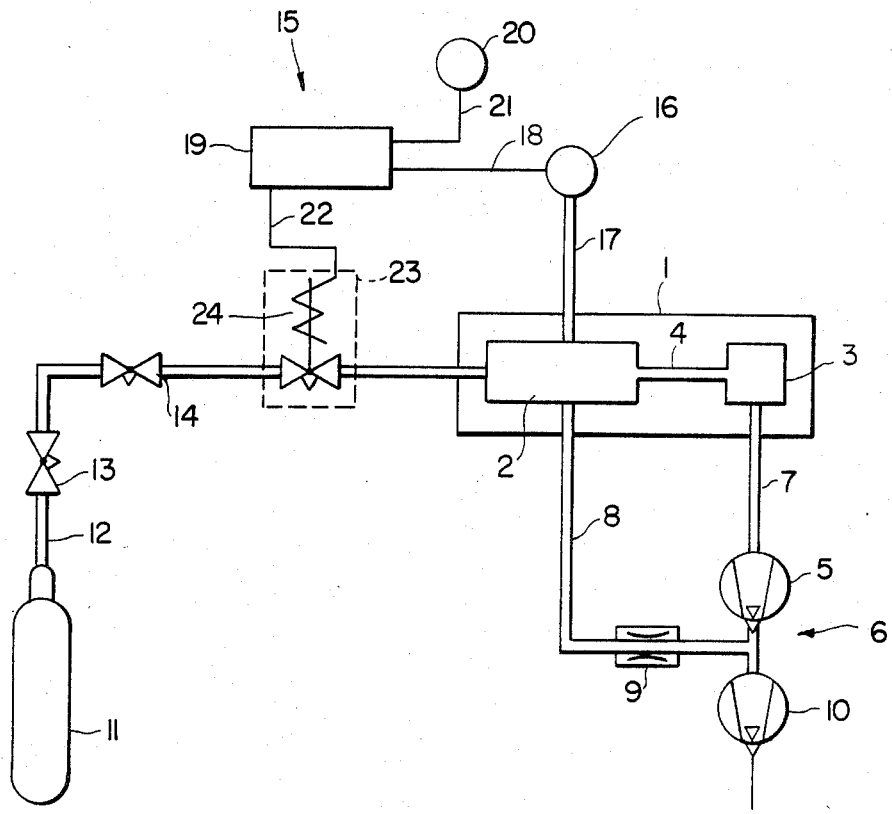

GLOW DISCHARGE TUBE FOR SPECTRAL-ANALYTICAL TESTS

BACKGROUND OF THE INVENTION

The present invention relates, in general, to a glow discharge tube for spectral-analytical tests, and more particularly to a system for improving the accuracy of conventional glow discharge tube systems.

German Pat. No. 1,589,389 and its Patent of Addition No. 1,910,461 disclose a glow discharge tube which is suitable for spectral-analytical tests. In the device disclosed therein, a tube is provided wherein a cathode glow light having a high luminous intensity is formed above the specimen, which is at the cathode potential. However, the glow light is limited by an annular anode support which extends to the specimen. The resulting annular gap between the end face of the anode support and the specimen probe forms a restricted path, or restrictor, between the anode, or main, cavity and the cathode cavity.

In the aforesaid German Patent and Patent of Addition the cathode cavity, or cathode space, of the glow discharge tube is evacuated until no glow discharge can arise therein. In the anode cavity, or anode space, a working pressure of a few millibars is established by means of a throttle valve fitted in the connecting line to the carrier gas source. With a voltage of approximately 1,000 to 1,500 v connected between the anode and the cathode, a glow discharge will be obtained with a current of about 100 to 200 mA. By maintaining the voltage, the current, or the power of the glow discharge tube at a constant value, perfectly linear and reproducible calibration curves are obtained for all the elements of the periodic system.

With conventional analytical concentrations in devices such as the foregoing, the margin of error in spectral-analytical tests lies distinctly below 1% relative to the specimen content. However, at the present time a number of applications, e.g., in the metallurgical industry, a still higher degree of accuracy is required.

SUMMARY OF THE INVENTION

It is, therefore, an object of the present invention to further improve on the performance of analytical systems using glow discharge tubes of the type described hereinabove and to achieve greater accuracy in the analytical results obtained by such systems.

The present invention achieves the foregoing object by feeding the carrier gas to the anode cavity while controlling the pressure in that cavity.

In the past, it was believed that the residual error in spectral analysis of a specimen was primarily caused by inaccuracies in the calibration of the system and/or by a lack of stability in the calibration over time, as well as by instabilities in the glow discharge. However, it has now been found that, surprisingly, even minor pressure variations from the ideal pressure of the carrier gas prevailing within the anode cavity are the cause of the residual margins of error in the emission spectral analysis performed by prior systems. Accordingly, by controlling the pressure of the carrier gas in the working space (i.e., within the anode cavity), the analytical accuracy is improved by a factor of approximately 5.

In a preferred embodiment of the present invention, therefore, a glow discharge tube system is provided wherein the main space, or anode cavity, of the tube is connected to a pressure transducer. The transducer provides an electrical output signal which is proportional to the measured pressure within the anode cavity. This output signal is applied to the first input of a comparator circuit, the second input of which is connected to, and receives the signal from, an ideal pressure value transmitter. The comparator compares the measured pressure value signal with the ideal pressure value signal and supplies a corrective output signal to an electrically controlled, continually adjustable valve located in the connecting line between a carrier gas source and the anode cavity.

Suitable pressure transducers and suitable valves capable of continual adjustment by electrical control signals, are well known in the art, and are not the subject matter of this invention.

BRIEF DESCRIPTION OF THE DRAWING

The foregoing, and additional objects, features and advantages of the present invention will become apparent to those of skill in the art from a consideration of the following detailed description of a preferred embodiment, taken in conjunction with the accompanying drawing in which the single figure is a schematic diagram of a glow discharge tube system in accordance with the present invention.

DESCRIPTION OF A PREFERRED EMBODIMENT

For simplicity in the drawings, only those parts of the glow discharge tube used in the present invention are illustrated which are essential for the operation thereof in the context of the present invention.

Referring now to the single figure of the drawing, a glow discharge tube 1 comprises an anode cavity, or main space, 2 and an adjacent cathode cavity 3. The two cavities are connected together by a restrictor passageway 4. The cathode cavity 3 is connected to the second stage 5 of a vacuum pump 6 by way of a passageway 7, the pump operating to evacuate the cathode cavity to a pressure of, for example, 0.3 millibar.

The anode cavity 2 is connected by way of a passageway 8 and a restrictor 9 to the first stage 10 of vacuum pump 6. The first stage of the vacuum pump produces a lesser vacuum than does the second stage, so that the pressure within the anode cavity 2 is greater than the pressure within the cathode cavity 3.

Spectrally pure argon gas is fed from a pressure cylinder 11 to the anode cavity 2 by way of passageway 12, which includes a pressure-reducing valve 13 followed by a manually adjustable throttle valve 14. Both valves are connected downstream of the pressure cylinder 11.

To regulate the pressure in the anode cavity 2 to a value of, for example, 3.0 millibar, an automatic control system is provided. The control system is composed of a pressure transducer 16 connected in communication with the anode cavity 2 by a passageway 17. The pressure transducer 16 delivers, on an output line 18, an electrical output signal which is proportional to the measured pressure within cavity 2. The output signal on line 18 is supplied to the first input of a comparator 19.

An ideal-value transmitter 20 provides at its output 21 an electrical signal corresponding to the ideal pressure which is to be maintained in the cavity 2, and this ideal signal is supplied to the second input of the comparator 19. An output signal is produced by the comparator which represents the difference between the measured pressure in cavity 2 and the desired ideal pressure. This comparator output signal, which appears on line 22, comprises a corrective signal.

Connected in passageway 12 downstream of valves 13 and 14, and between these valves and the cavity 2, is an electrically-controlled, continually adjustable flow control valve 23. The electrically-controlled valve may, for example, be operated by a solenoid 24 to produce a change in its flow cross-section which is proportional to the corrective signal applied thereto by way of line 22. The output line 22 of the comparator 16 is connected to the controllable valve, whereby the output signal from the comparator corrects the setting of valve 23 to maintain the ideal pressure in cavity 2.

What is claimed is:

1. A glow discharge tube for spectral-analytical tests, having an anode space which is connected on one side to a carrier gas source and, on the other, to a first vacuum pump, and which communicates via a restrictor with a cathode space connected to a second vacuum pump which produces a relatively high vacuum, characterized in that the carrier gas is fed to the main space while its pressure is being controlled.

2. The glow discharge tube as defined in claim 1, characterized in that the main space is connected to a pressure transducer whose pressure-proportional electrical output signal is applied to the first input of a comparator, whose second input receives the signal of an ideal-pressure value transmitter, and whose output supplies a control signal for an electrically controlled, continually adjusted valve placed in the tubing connecting the main space with the carrier gas source.

3. A glow discharge tube system for spectral-analytical tests, comprising:
   an anode cavity;
   a cathode cavity connected to said anode cavity through a restricted passageway;
   an electrically controllable valve;
   a carrier gas source connected through said controllable valve to supply carrier gas to said anode cavity;
   first vacuum pump means connected to said anode cavity to produce a first pressure level therein;
   second vacuum pump means connected to said cathode cavity to produce a second pressure level therein, said second pressure level being less than said first pressure level; and
   control means for operating said controllable valve to maintain the pressure level within said anode cavity at a predetermined value.

4. The glow discharge tube system of claim 3, wherein said control means includes:
   a pressure transducer connected to said anode cavity to measure and to produce an output signal proportional to the pressure in said anode cavity;
   an ideal pressure signal source;
   comparator means for receiving and comparing said output signal and said ideal pressure signal to produce a corrective signal corresponding to the difference between the measured pressure within said anode cavity and an ideal pressure for said anode cavity; and
   means connecting said corrective signal to said controllable valve to adjust the flow of said carrier gas to said anode cavity to maintain the ideal pressure in said anode cavity.

5. A system for spectral-analytical tests, comprising:
   a glow discharge tube having an anode space, a cathode space, and restrictor means, said anode space communicating with said cathode space by way of said restrictor means;
   connection means for connecting a first side of said anode space to a carrier gas source for continuously supplying gas to said anode space;
   a first vacuum source;
   means connecting a second side of said anode space to said first vacuum source;
   a second vacuum source which produces a relatively high vacuum with respect to said first vacuum source; and
   means connecting said cathode space to said second vacuum source.

6. The system of claim 5, further including means for controlling the pressure of said anode space.

7. The system of claim 6, wherein said means for controlling the pressure in said anode space includes said connection means.

8. The system of claim 7, wherein said means for controlling the pressure in said anode space further includes pressure transducer means connected to said anode space, and control means responsive to said transducer for regulating said connection means.

9. The system of claim 6, wherein said means for controlling the pressure in said anode space includes:
   a pressure transducer connected to said anode space to produce a pressure-proportional output signal;
   a comparator having first and second inputs, said first input receiving said pressure-proportional output signal and said second input receiving an ideal-pressure value signal, said comparator producing a pressure control signal responsive to said first and second inputs;
   said connection means include an electrically controlled, continually adjustable valve responsive to said pressure control signal to control the pressure in said anode space.

* * * * *